(12) United States Patent
Kaito et al.

(10) Patent No.: US 11,950,821 B2
(45) Date of Patent: Apr. 9, 2024

(54) SURGICAL TOOL FOR POSITIONING A SURGICAL DEVICE, SURGICAL DEVICE AND KIT

(71) Applicant: MEDACTA INTERNATIONAL SA, Castel San Pietro (CH)

(72) Inventors: Takashi Kaito, Castel San Pietro (CH); Keitaro Matsukawa, Castel San Pietro (CH); Geert Mahieu, Castel San Pietro (CH); Ralph Mobbs, Castel San Pietro (CH); Yuichiro Abe, Castel San Pietro (CH); Meinrad Fiechter, Castel San Pietro (CH); Francesco Siccardi, Castel San Pietro (CH); Gianluca Milano, Castel San Pietro (CH)

(73) Assignee: Medacta International SA, Castel San Pietro (CH)

( * ) Notice: Subject to any disclaimer, the term of this patent is extended or adjusted under 35 U.S.C. 154(b) by 429 days.

(21) Appl. No.: 17/297,096

(22) PCT Filed: Nov. 21, 2019

(86) PCT No.: PCT/IB2019/060020
§ 371 (c)(1),
(2) Date: May 26, 2021

(87) PCT Pub. No.: WO2020/109940
PCT Pub. Date: Jun. 4, 2020

(65) Prior Publication Data
US 2022/0008109 A1  Jan. 13, 2022

(30) Foreign Application Priority Data
Nov. 26, 2018 (IT) .......................... 102018000010562

(51) Int. Cl.
*A61B 17/88* (2006.01)
*A61B 17/16* (2006.01)
*A61B 17/00* (2006.01)

(52) U.S. Cl.
CPC ...... *A61B 17/8886* (2013.01); *A61B 17/1655* (2013.01); *A61B 2017/00389* (2013.01); *A61B 2017/00477* (2013.01)

(58) Field of Classification Search
CPC .................. A61B 17/8886; A61B 2017/00389
See application file for complete search history.

(56) References Cited

U.S. PATENT DOCUMENTS 8,048,129 B2 * 11/2011 Forton ............... A61B 17/7083
606/252
9,801,667 B2 * 10/2017 Hawkes ............. A61B 17/7086
(Continued)

OTHER PUBLICATIONS

International Search Report and Written Opinion for International Application No. PCT/IB019/060020 dated Feb. 11, 2020, 17 pages.

*Primary Examiner* — Christian A Sevilla
(74) *Attorney, Agent, or Firm* — Meunier Carlin & Curfman LLC

(57) ABSTRACT

A surgical tool for positioning a surgical device includes a gripping portion; a rod protruding from the gripping portion; and a coupling system. The coupling system comprises an axial retention assembly comprising, at a free end of the rod, two opposite semispherical portions, wherein respective flat surfaces are separated from each other by an axial notch made partially along the rod, and a central clutch movable between a locking position and a disengagement position. In the locking position, the central clutch approaches the free end of the rod and is interposed between the two semispherical portions, preventing reciprocal approach thereof so as to block the two semispherical portions within a seat of said surgical device. In the disengagement position, the central
(Continued)

clutch moves away from the free end such that the two semispherical portions can approach to allow the tool to come out of the surgical device.

9 Claims, 8 Drawing Sheets

(56) References Cited

U.S. PATENT DOCUMENTS

| | | | |
|---|---|---|---|
| 2004/0147928 A1* | 7/2004 | Landry | A61B 90/92 |
| | | | 606/264 |
| 2011/0202096 A1* | 8/2011 | White | A61B 17/8685 |
| | | | 606/86 R |
| 2011/0257690 A1 | 10/2011 | Rezach | |
| 2012/0239092 A1* | 9/2012 | Jones | A61B 17/8866 |
| | | | 606/279 |
| 2012/0247284 A1 | 10/2012 | Murray et al. | |
| 2013/0150864 A1 | 6/2013 | Marik et al. | |
| 2013/0331891 A1* | 12/2013 | Bergeron | A61B 17/1655 |
| | | | 606/272 |
| 2015/0250521 A1 | 9/2015 | Poker et al. | |

* cited by examiner

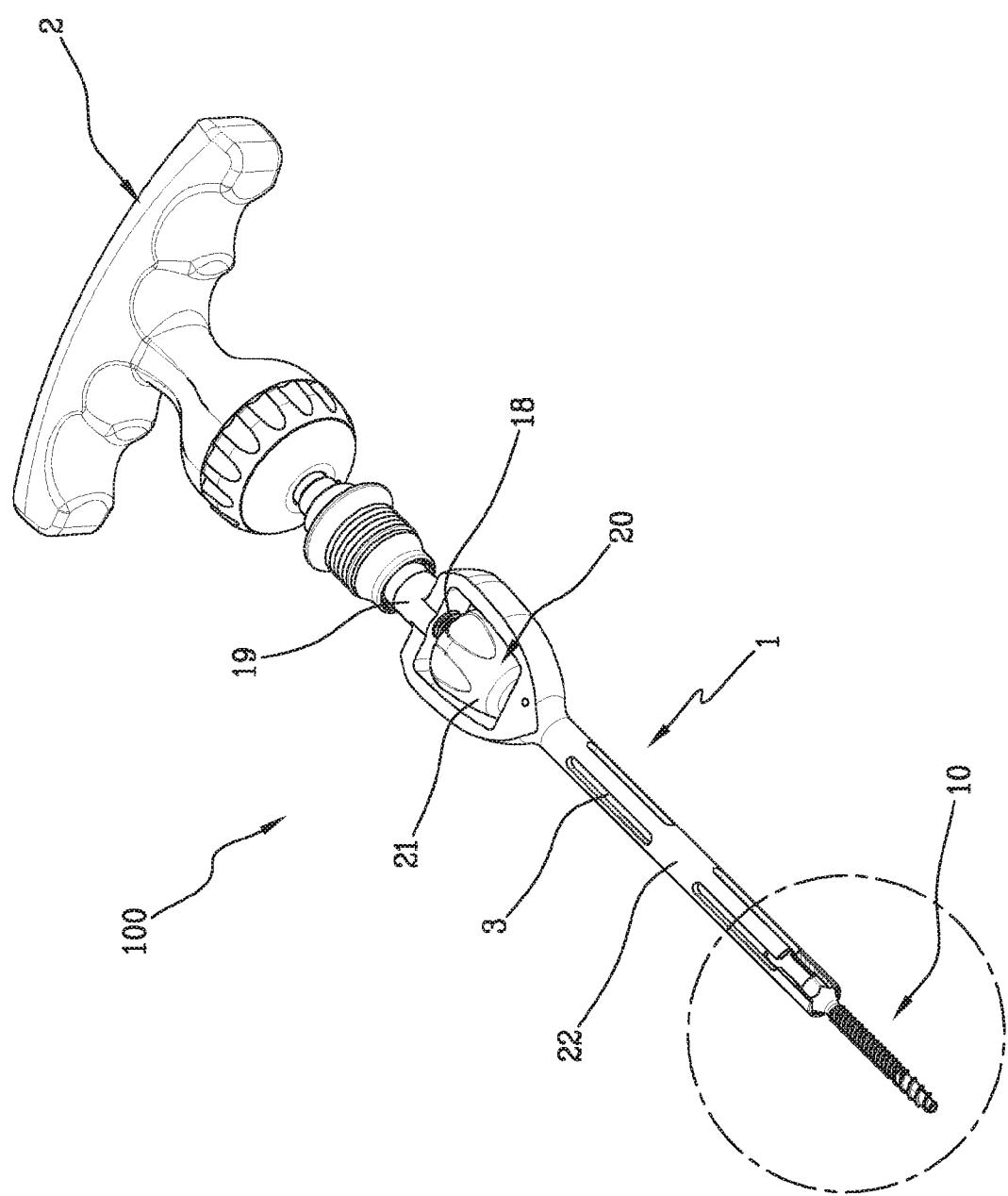

SURGICAL TOOL FOR POSITIONING A SURGICAL DEVICE, SURGICAL DEVICE AND KIT

TECHNICAL FIELD

This invention concerns a surgical tool for positioning a surgical device which is adapted for being used in a patient, a surgical device that can be coupled to that surgical tool and a kit for positioning said surgical device. In particular, the surgical device that is the subject of this invention is, for example, a tapping attachment, or a screw, or any other tool that can be inserted into a patient and is equipped with a coupling and movement head. The surgical tool, in turn, is adapted to act on this device to position it correctly and engage it inside the patient or to move it as required.

PRIOR ART

There are known surgical tools such as screwdrivers, retractors, or the like that interact with surgical devices such as tapping attachments, screws, or the like to position them by screwing them inside vertebrae or bone structures or that interact with them to dislocate vertebrae from their original position.

The known surgical devices have a gripping head generally comprising a polygonal—e.g. hexagonal—external profile to be grasped and moved in rotation by instruments similar to compass screwdrivers or having a notch for interacting with flat-headed screwdriver tips or blade heads such as those of retractors or other surgical instruments.

In the first case (head with polygonal external profile) the rotational coupling is guaranteed: the tool is able to couple with the surgical device to screw it into its seat once the surgeon has positioned it inside the patient.

The surgeon must place the device free-handed in position in a site that has body fluids, soft tissues, and very little space for manoeuvre.

There is a high risk that the surgical device will escape the surgeon's hands or that its correct positioning in the seat, and its subsequent coupling to the tool, will be complicated.

In addition, the manual positioning inevitably requires more operating space to allow the surgeon to handle the tapping attachment or screw with their fingers, for example, and to position them in contact with the vertebrae: the wound will also be widened. The device must then be held in place with the hands to engage it with the tool or left free if there is not enough space, with the risk that it may move from its correct position.

Alternatively, when using other tools, such as a vertebral retractor, the screws that are already positioned and secured to the vertebrae must be engaged by the retractor tips that interfere with the pedicle screw tulip. This operation may not be very stable and requires extreme manual skill on the part of the surgeon.

The applicant therefore encountered the need for an axial engagement system between the tool and the device that allows the surgeon to insert the device inside the patient directly with the tool, without the risk of the two disengaging, or a secure coupling that allows easier and safer manoeuvrability and interaction between the tool and the surgical device. In addition, the tapping attachment is used to create the path via which the implant is then inserted, such as a pedicle screw.

The tapping attachment is a screw, generally with a double thread, adapted to make the hole inside which the pedicle screw is then inserted, which will then remain in situ.

The tapping attachment generally has a stem with a diameter slightly smaller than that of the screw that then, with its thread, interacts with the bone and couples itself to the walls of the same in a stable manner.

Currently, the tapping devices dedicated to this function are monoblock devices: once the "tapping" surgical manoeuvre is complete, the device is removed, leaving the channel in the bone open with possible loss of blood. The implant is then inserted through this channel to be able to proceed with standard surgical manoeuvres (distraction, discectomy, etc. . . . ). The tapping attachment has in fact the sole purpose of creating the channel for inserting the implant, without any possibility of allowing even the standard surgical manoeuvres mentioned above. However, the overall size of the implant (consisting of two main components: the stem or pedicle screw and the head or tulip) may hinder the proper execution of subsequent surgical manoeuvres.

Therefore, the need arose to have a surgical device, such as a tapping attachment, that directly allows surgical manoeuvres to be undertaken, which were hitherto impossible to perform with a normal tapping attachment, without the need to place a classic pedicle screw in situ.

The purpose of this invention is to overcome the disadvantages encountered in currently known surgical tools and devices.

Therefore, the purpose of this invention is to provide a surgical device that can be used for surgical manoeuvres without hindering their proper execution.

Another purpose of this invention is to present a device that, once positioned, serves both as a plug for possible blood loss and as an anchorage to the bone in order to proceed with standard surgical manoeuvres.

Furthermore, the purpose of this invention is to propose a surgical tool that can be easily used with said surgical device and that also allows an axial engagement to be created with the latter.

Finally, the purpose of this invention is to propose a kit for positioning a surgical device that allows the creation of an axial engagement system between the tool and the device, facilitating the insertion of the latter inside the patient without the risk of their reciprocally disengaging, so as to speed up the surgical time and facilitate the positioning manoeuvres for the surgeon.

These and other purposes are achieved by a surgical tool for positioning a surgical device adapted for being engaged in a patient, by a surgical device that can be coupled to that surgical tool, and by a kit for positioning said surgical device as claimed herein.

SUMMARY

In particular, according to a first aspect, this invention concerns a surgical tool for positioning a surgical device comprising a gripping portion, a rod protruding from the gripping portion along a main development direction of the tool up to its free end and a coupling system adapted to being coupled with a surgical device that can be engaged with a patient and is operatively active at the free end.

Advantageously, the coupling system comprises an axial retention assembly comprising, at the free end of the rod, two opposite semispherical portions, facing each other for their respective flat surfaces, separated from each other by an axial notch made partially along the rod. The restraint system comprises, in addition, a central clutch which is selectively movable between a locking position, in which the central clutch approaches the free end of the rod and is interposed between the two semispherical portions, preventing the reciprocal approach thereof so as to block the two semispherical portions inside a seat of the surgical device, and a disengagement position, in which the central clutch moves away from the free end of the rod and at which the two semispherical portions can approach each other to allow the tool to come out of the surgical device. Advantageously, the seat of the surgical device inside which the coupling system is inserted is a semispherical cavity counter-shaped to the two semispherical portions when free to approach. In this way, when the clutch is interposed between them, it pushes them radially outwards, preventing them from coming out of the semispherical cavity present in the surgical device. This prevents the tool and the surgical device from being axially disengaged.

The coupling system also comprises a nut screw adapted to interact with a threaded portion of the clutch to promote its axial translation. Advantageously, the nut screw is integral with the gripping portion.

The surgical tool also comprises movement means directly active on the central clutch to axially rotate it.

The movement means preferably comprise a driving handwheel that is integral with the central clutch.

The coupling system advantageously comprises a rotational engaging assembly comprising a sleeve protruding from the gripping portion along the tool's main development direction up to its free end, which has a polygonal internal profile that can be engaged with the internal profile of the surgical device, which also has a corresponding polygonal shape The sleeve contains the above-mentioned rod inside.

In a second aspect, this invention concerns a surgical device comprising a gripping head with a semispherical cavity adapted to be engaged with the coupling system of the surgical tool.

This gripping head has a polygonal external profile, adapted to be engaged with a corresponding polygonal profile of the coupling system of the surgical tool.

The surgical device also has a stem with a first and a second external thread. These threads have different pitches to each other.

In a third aspect, the invention also concerns a kit for positioning a surgical device comprising a surgical tool as described above and at least one surgical device with a head that can be coupled with the coupling system of the surgical tool.

Additional characteristics and benefits will be more apparent from the dependent claims and from the detailed description of a preferred, but not exclusive, embodiment of a surgical tool, a surgical device, and a kit for positioning a surgical device via a surgical tool, according to this invention.

BRIEF DESCRIPTION OF THE DRAWINGS

This invention will be made clearer by the following detailed description, with reference to the attached drawings provided by way of example only, wherein:

FIG. 4 shows a perspective view of a kit for positioning a surgical device via a surgical tool in accordance with this invention;

FIG. 6b shows an enlarged view of a detail from FIG. 6a;

DETAILED DESCRIPTION

Figure 1:
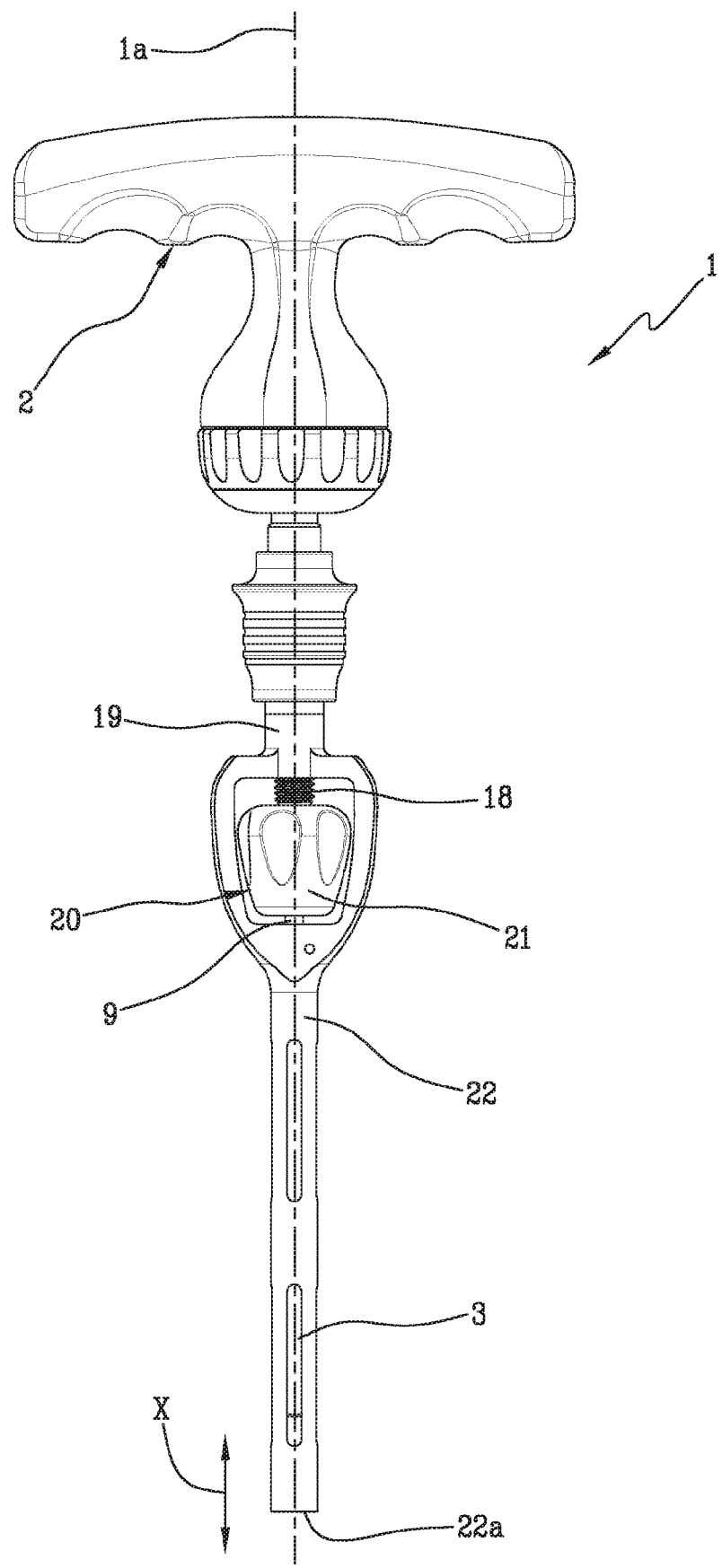
FIG. 1 shows a front view of a surgical tool in accordance with this invention.
Figure 2:
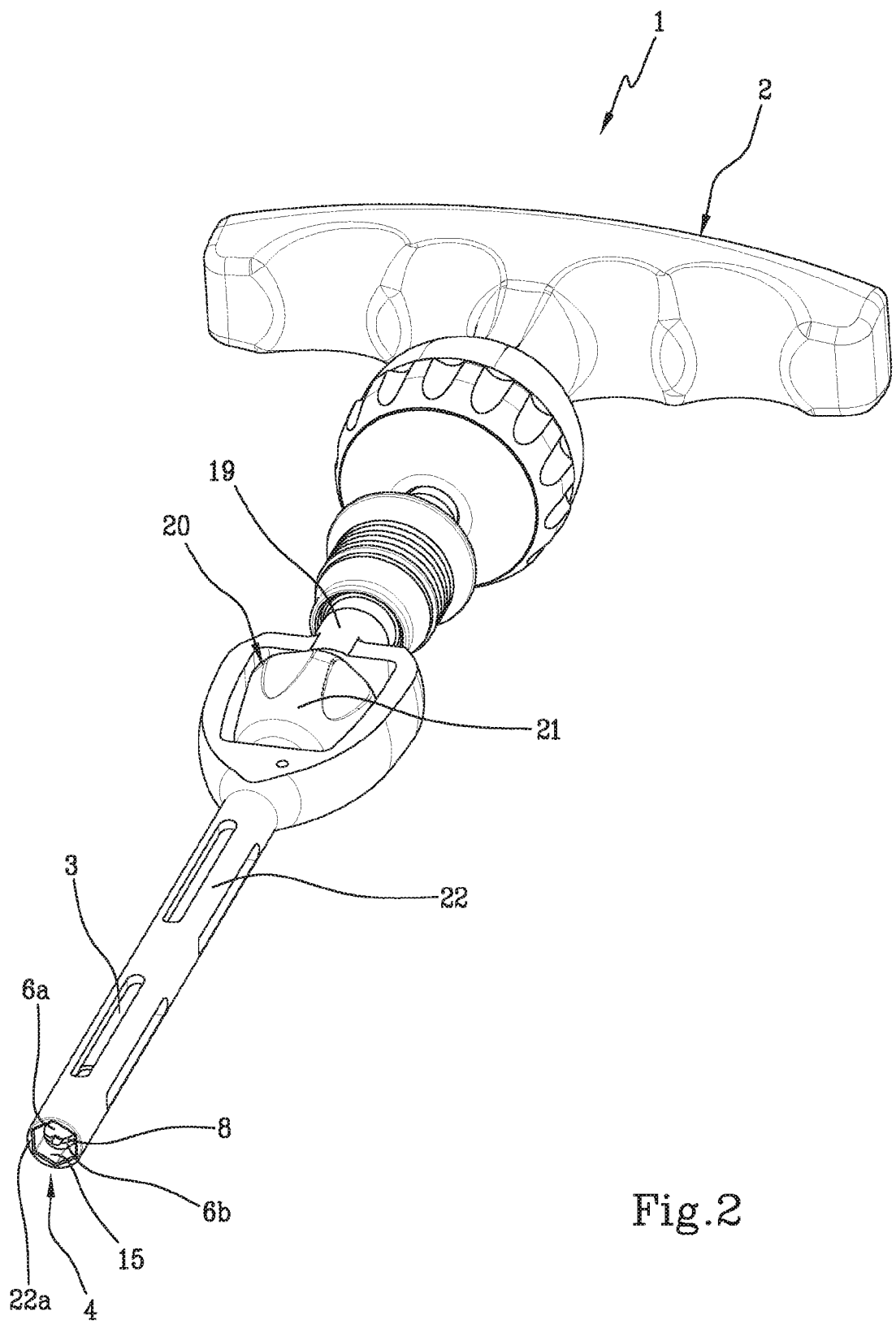
FIG. 2 shows a perspective view of the surgical tool shown in FIG. 1.

In the above figures, the number 1 designates in its entirety a surgical tool for the positioning of a surgical device, according to this invention.

The surgical tool 1 comprises a gripping portion 2 from which a rod 3 extends along a main development direction X coinciding with the axis 1a of the tool 1. The rod 3 extends from the gripping portion 2 up to its own free end 3a.

Figure 3A:
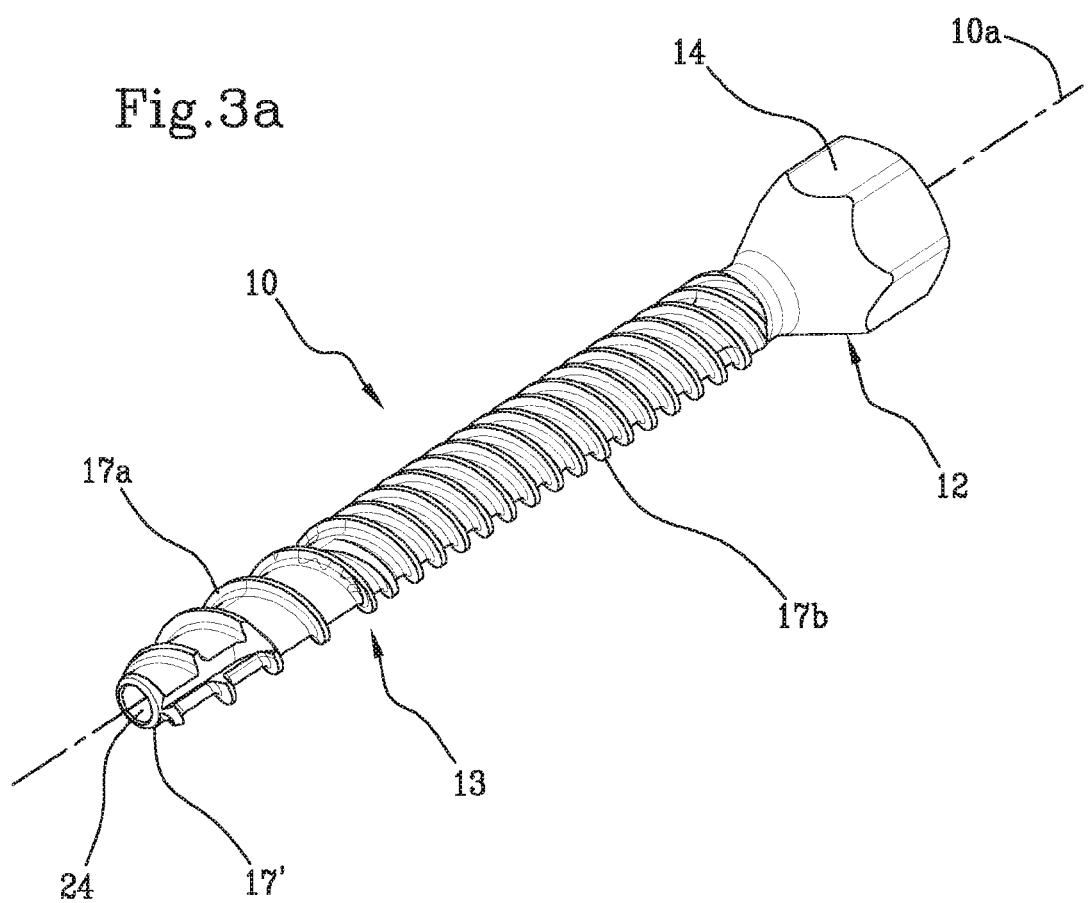
FIGS. 3a and 3b show two perspective views of the surgical device in accordance with this invention.
Figure 3B:
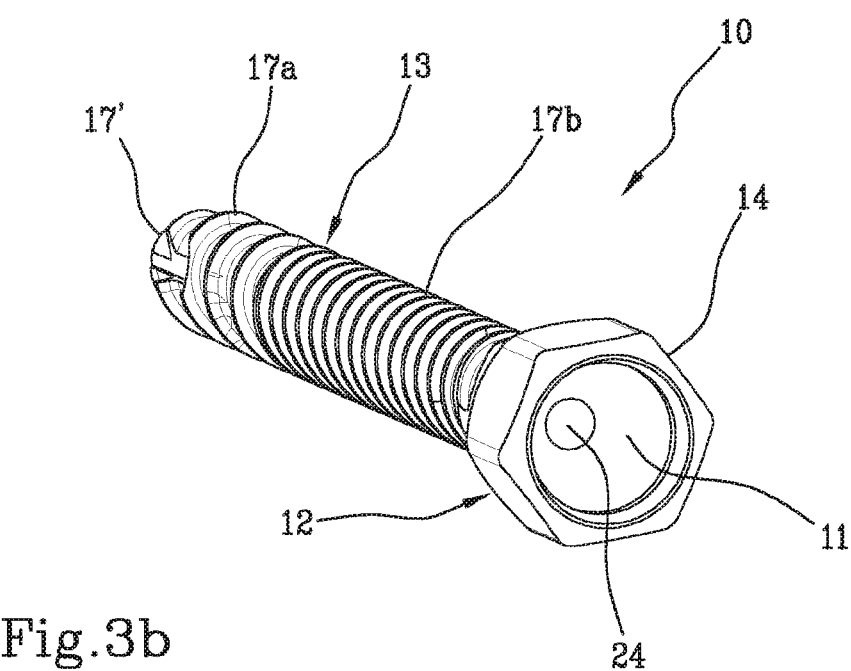
Figure 5:
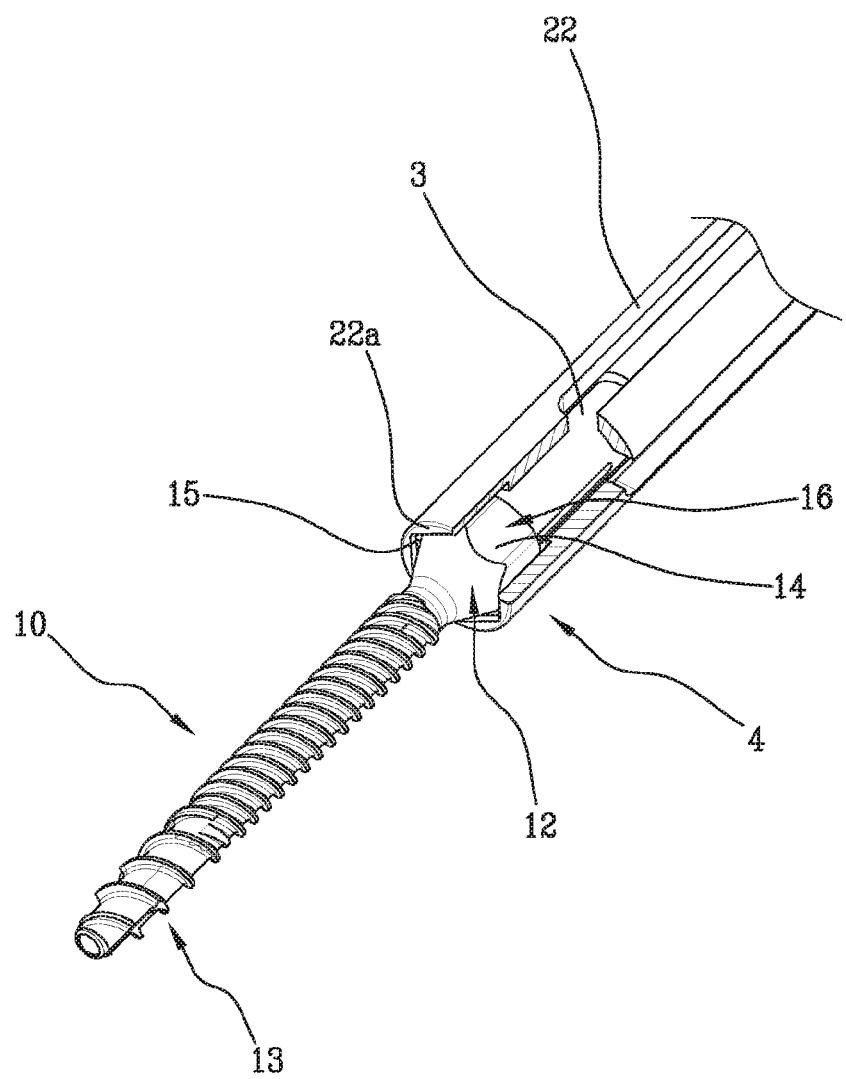
FIG. 5 shows an enlarged and partially sectioned detail of the kit illustrated in FIG. 4.
Figure 6A:
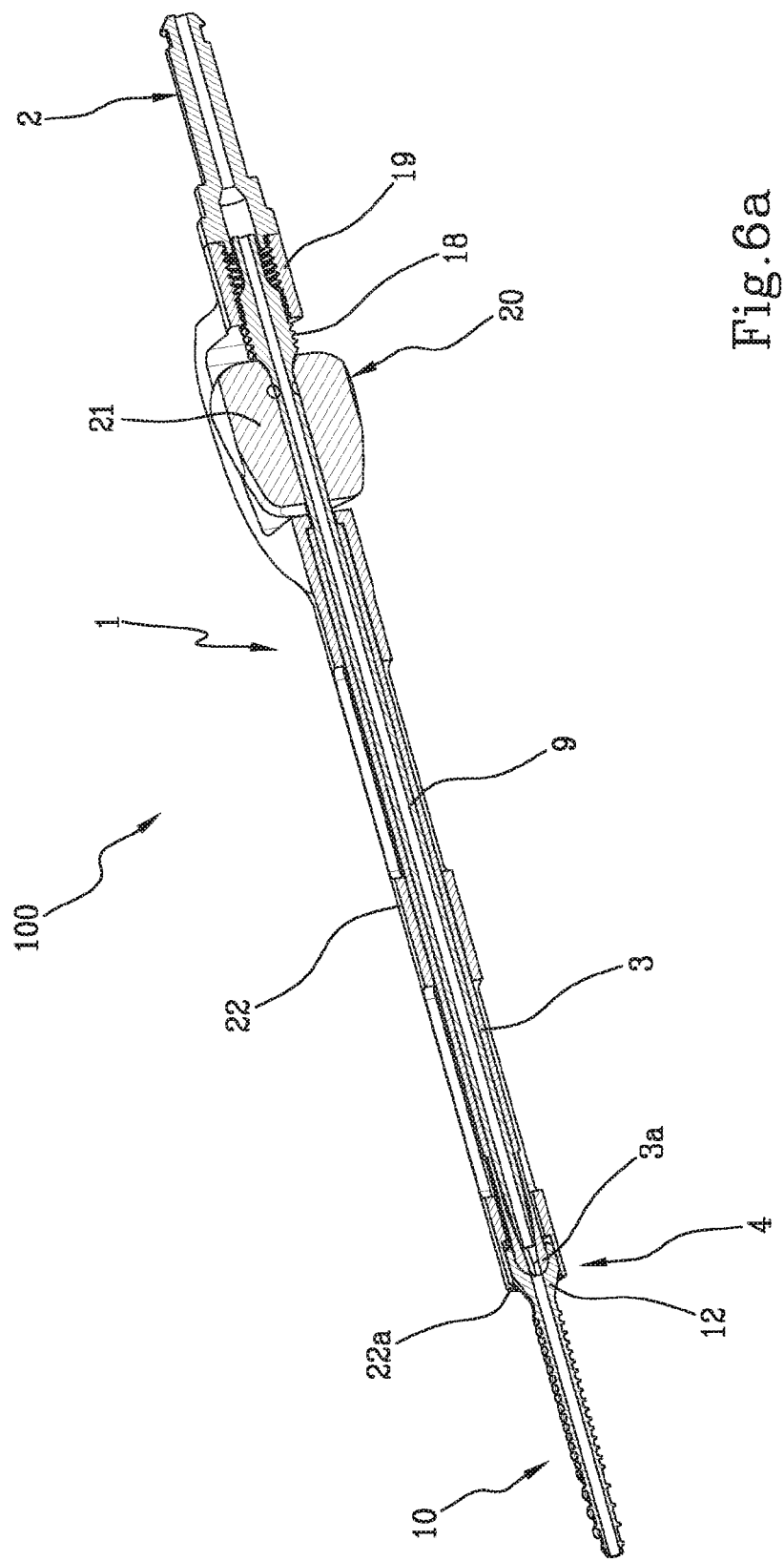
FIG. 6a shows a sectioned perspective view along the development axis of the kit shown in FIG. 4.
Figure 6B:
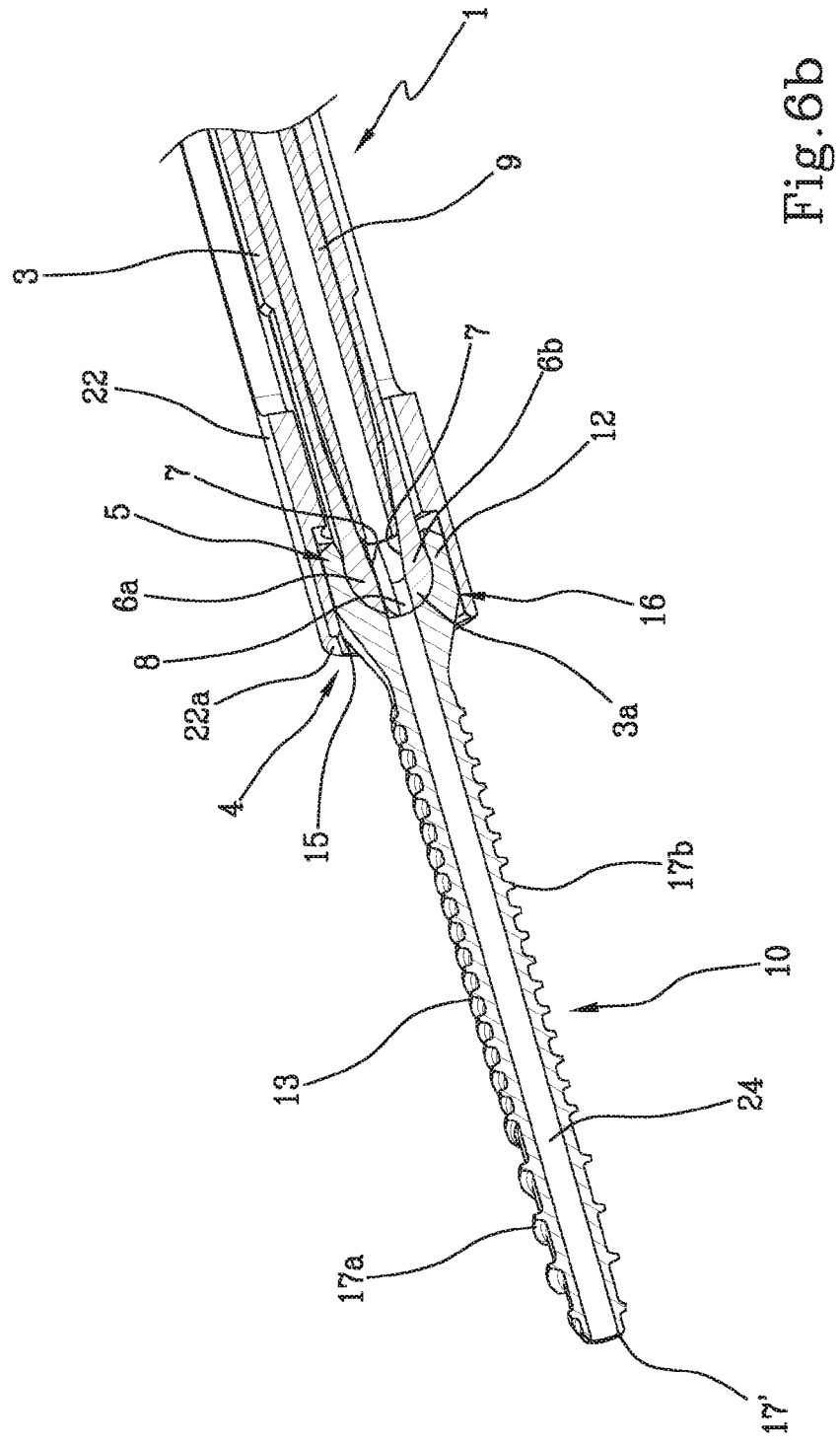

The tool 1 also comprises a coupling system 4 adapted to be coupled with a surgical device 10, represented in FIGS. 3a and 3b, which can be engaged with a patient and is operatively active at the free end 3a of said rod 3.

The surgical device 10 is, for example, a tapping attachment or a polyaxial screw and has a gripping head 12 and a stem 13.

As shown in FIGS. 3a and 3b, the gripping head 12 is shaped so as to connect with the above-mentioned coupling system 4. In particular, it has a semispherical cavity 11 adapted to be engaged with an axial retention assembly 5 of the coupling system 4 of the surgical tool 1, as described below. In addition, the gripping head 12 also has a polygonal external profile 14 adapted to be engaged with a rotational engaging assembly 16 of the coupling system 4, having a corresponding polygonal internal profile 15, as will be described below in more detail.

The surgical device 10, in addition, comprises a stem 17 having a first 17a and a second 17b external thread. The first 17a and the second 17b external threads have different pitches from each other: in particular, the first thread 17a, the one closest to the free end 17' of the stem, opposite to the head 12, is greater than the second thread 17b interposed between the first thread 17a and the head 12 of the surgical device.

In the case of tapping, in fact, there is the need to make a first penetration into the bone having a thread with a larger pitch so as to have a higher feed rate equal to the revolutions of the tool. Following this, a thread with the same pitch as the screw follows, which will then be positioned in place of the tapping attachment.

Advantageously, the tapping attachment has a central axial cavity 24 that places the semispherical cavity 11 in fluidic connection with the free end 17'. This central axial cavity 24 can be used for inserting Kirschner wires, or the like.

Returning now to the surgical tool 1, the coupling system 4 can be engaged inside a semispherical cavity 11 present in the surgical device 10, in particular in the semispherical cavity 11 obtained in the head 12 of the surgical device 10, which can be seen in FIG. 3b.

The coupling system 4 is used, when used for the first time, to ensure that the tool 1 axially retains the device 10, and to prevent the device from accidentally coming out, once it has been coupled, unless the connection is deactivated.

For this purpose, the coupling system 4 comprises an axial retention assembly 5 that comprises, at the free end 3a of said rod 3, two opposite semispherical portions 6a and 6b, facing each other for their respective flat surfaces 7. The two semispherical portions, in particular the two facing surfaces 7, are separated from each other by an axial notch 8 partially made along the axis 1a of the rod 3.

In other words, at the free end 3a, the rod 3 has an axial notch 8 that divides the free end 3a into two semispherical portions 6a and 6b facing each other. Internally, the rod 3 has an axial channel inside of which a central clutch 9 is slidably inserted.

The central clutch 9 is selectively movable between a locking position, in which it approaches the free end 3a of the rod 3 and is interposed between the two semispherical portions 6a and 6b preventing their reciprocal approach, and a disengagement position, in which it moves away from the free end 3a of the rod 3 and at which the two semispherical portions 6a and 6b may approach to allow the tool to come out of the surgical device 10. The free end 3a of the rod 3, in particular the two semispherical portions 6a and 6b, are inserted inside the semispherical cavity 11 of the head 12 of the surgical device 10, slightly approaching each other.

By sliding the clutch and interposing it between the two semispherical portions, they can no longer approach each other but remain spaced apart and pushed radially outwards: this prevents the free end 3a from coming out of the semispherical cavity 11 of the head 12.

In other words, by exerting a light thrust, the free end 3a' is inserted via an intervention into the semispherical cavity 11. During this operation, the two semispherical portions 6a and 6b tend to approach each other to pass through the outer circular edge of the semispherical cavity.

By activating the axial retention assembly 5, the clutch is axially advanced towards the free end 3a, interposing itself between the two semispherical portions and filling the gap between them, preventing them from approaching each other. Thus, the tool cannot come out axially from the device because to do so the two semispherical portions would have to approach each other in order to pass through the external circular edge of the semispherical cavity of the head of the surgical device.

The axial engagement between the tool and the device is thus guaranteed.

To promote axial translation, the central clutch 9 has a threaded portion 18 interacting with a nut screw 19.

In particular, the coupling system 4 comprises a nut screw 19 adapted to interact with the threaded portion 18 of the central clutch 9. In particular, as shown in FIG. 1, the nut screw 19 is integral with the gripping portion 2 of the tool 1. The nut screw 19 can, preferably, be integral with and an integral part of the load-bearing or protective outer structure of the tool 1.

To move it more easily, there are also movement means 20 directly active on the central clutch 9 to axially rotate it. In detail, the movement means 20 comprise a driving handwheel 21 integral with the central clutch 9. The driving handwheel 21 can be welded, made of one piece, or connected via a clutch pin 9. By rotating the handwheel 21, the rotation is also transmitted to the central clutch 9; following the rotation, the threaded portion 18 interacts with the nut screw 19 promoting the axial translation of the central clutch 9 in one direction or the other.

In a second use, the coupling system 4 serves to move the device 10, so as, for example, to promote the rotation of the device 10 around its rotation axis 10a, and to position it correctly inside the patient.

In the case, therefore, of a tapping attachment or pedicle screw, the tool acts as a screwdriver to screw the surgical device into the bone.

To achieve this second use, the coupling system 4 also comprises a rotational engaging assembly 16. This rotational engaging assembly 16 comprises a sleeve 22 protruding from the gripping portion 2 along a development direction X of the main tool up to its own free end 22a.

The sleeve 22 is internally hollow and contains the above-mentioned rod 3 that slides inside it.

The sleeve 22, at its free end 22a, has a polygonal internal profile 15 that can be engaged with the surgical device 1. In particular, the polygonal internal profile 15 of the sleeve 22 can be engaged with the polygonal external profile 14 of the head 12 of the surgical device 10.

The set of the surgical tool 1 and of at least one surgical device 10, in accordance with what is described in this invention, defines a kit 100 for positioning a surgical device.

In use, when the surgeon has to position a surgical device, such as a tapping attachment or a pedicle screw, which has to be positioned inside a bone, they prepare the tool 1 by first acting on the driving handwheel 21, so that the central clutch 9 is moved away from the free end 3a of the rod 3. Thus, the clutch is not interposed between the two semispherical portions 6a and 6b, which can, thus, approach each other and be inserted inside the semispherical cavity 11 of the head 12.

The surgeon then connects the head 12 of the device to the coupling system 4, in particular they insert the free end 3a of the rod 3 of the axial retention assembly 5 into the semispherical cavity 11 of the head 12, exerting slight pressure.

The polygonal external profile 14 of the head 12 is inserted inside the free end 22a of the sleeve 22, matching the polygonal internal profile 15 of the free end 22a of the sleeve itself.

At this point, the surgeon acts again on the handwheel 21 by rotating it. The screw-leadscrew coupling between the threaded portion 18 of the central clutch 9 and the nut screw 19 connected to the gripping portion of the tool transforms the rotation of the handwheel 21 into an axial translation of the central clutch 9. Using the handwheel 21, the central clutch 9 advances towards the free end 3a of the rod 3, interposing itself between the two semispherical portions 6a and 6b of the rod 3. The presence of the central clutch 9 between the two semispherical portions 6a and 6b prevents the latter from approaching and, on the contrary, exerts a slight thrust in the external radial direction, moving the two semispherical portions away from each other. Thus, the two semispherical portions tend to widen inside the semispherical cavity of the head of the device, preventing the tool from coming out and disengaging the surgical device, which becomes an extension of the tool itself and can thus be easily handled.

Once the axial engagement is assured, the tool can be used as a normal screwdriver: the coupling between the two external and internal polygonal profiles respectively of the device head and of the sleeve ensures the rotational engagement: by rotating the tool, the device is also rotated, which can be screwed into its seat.

Once the device is inserted into the bone, the tool can be removed by acting again on the movement means, then on the handwheel, which moves the clutch away from the free end of the rod, making the two semispherical portions free, again, to approach each other. By pulling the tool with a light force, it detaches itself from the device.

The particular constraint and connection mechanism between the head of the surgical device, and in particular the semispherical cavity present in the device head, and the particular geometry of the axial retention assembly comprising the two semispherical portions, is adapted to easily act on the devices placed in position with subsequent surgical manoeuvres, without the need to remove, for example, the tapping attachment and to immediately position the pedicle screw.

In fact, during a normal surgical operation that involves, for example, the distraction of two vertebrae, usually at least a couple of tapping attachments are inserted to make respective holes that are then removed to be replaced by pedicle screws. The retractor acts on the screws with many drawbacks due to the larger size of the screw heads and an unstable interaction between retractors and screws.

By instead adopting the engagement system described in this invention—in particular the use of surgical devices comprising heads equipped with semispherical cavities and tools with tips with two semispherical portions, adapted for being inserted by interlocking inside the semispherical cavity—the drawbacks encountered in the previous technique are resolved.

Figure 7:
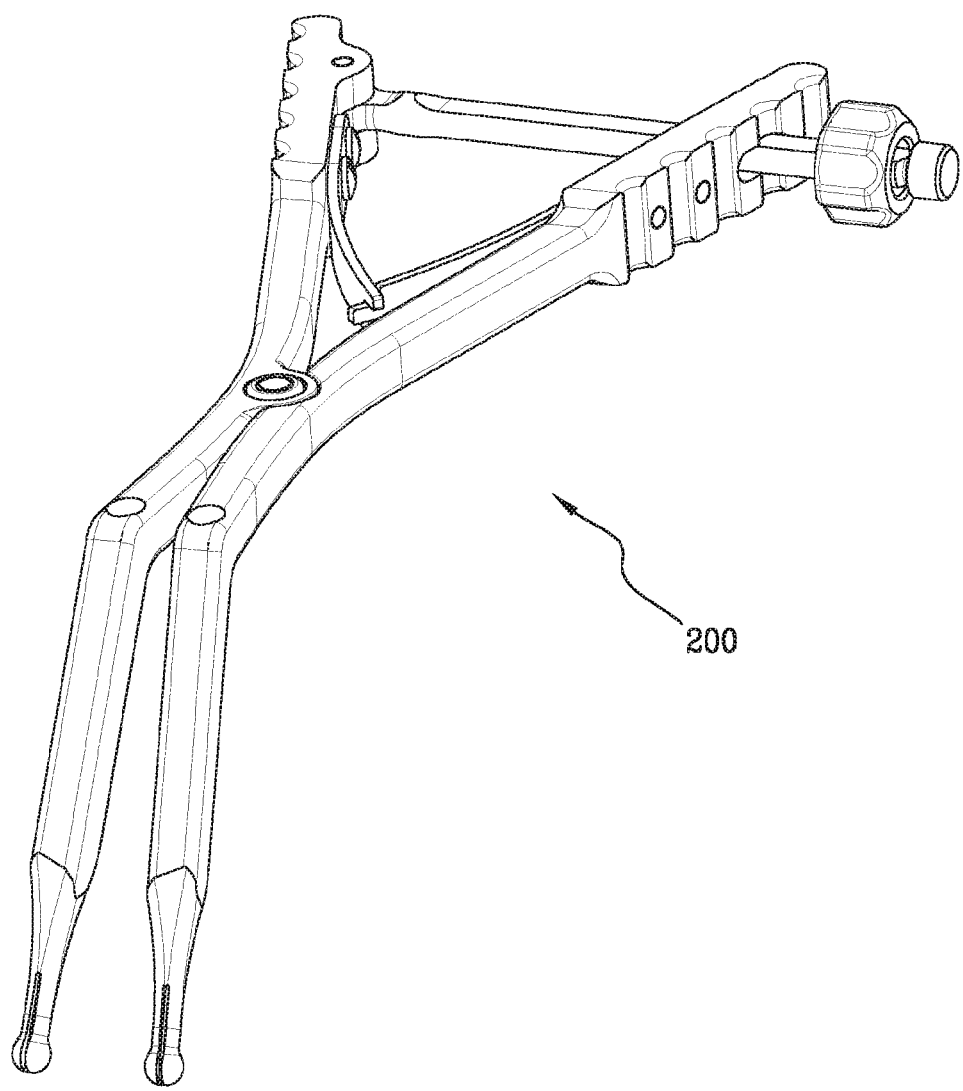
FIG. 7 shows an example of a surgical instrument that can be coupled with the device that is the subject of this invention.

One example of such a surgical tool is shown in FIG. 7, where a retractor 200 is represented the tips of which are each made with two semispherical portions adapted for being inserted inside devices such as the one covered by this invention. The retractor may also comprise the axial retention assembly, not shown in FIG. 7.

The interaction between the tool and the device ensures the very important axial engagement for the installation of the device itself, avoiding the need for preliminary manual manoeuvres to position the tapping attachment or the screw.

This makes it possible to create an axial engagement between the tool and the device, so that the device becomes an extension of the tool, greatly facilitating operations for the surgeon.

The special shape of the head of the device allows the device to be used for subsequent standard surgical manoeuvres as well, without the need to remove the first device, with the risk of blood loss, to position the device designed for subsequent surgical manoeuvres. In detail, a tapping attachment can also be used for distraction manoeuvres between vertebrae using a retractor equipped with a tip designed to interact with the head of the tapping device already positioned.

The invention claimed is:

1. A surgical tool for positioning a surgical device, the surgical tool comprising:
    a gripping portion;
    a rod protruding from said gripping portion along a main development direction of the tool up to a free end of the rod;
    a coupling system adapted to be coupled to a surgical device which can be engaged with a patient and the coupling system being operatively active at said free end;
    said coupling system comprising an axial retention assembly comprising, at said free end of said rod, two opposite semispherical portions, wherein respective flat surfaces of the semispherical portions face each other and are separated from each other by an axial notch made partially along said rod, and said coupling system comprising a central clutch which is selectively movable between a locking position, in which the central clutch approaches the free end of said rod and is interposed between the two semispherical portions, preventing reciprocal approach thereof so as to block said two semispherical portions within a seat of said surgical device, and a disengagement position, in which the central clutch moves away from the free end of said rod and at which the two semispherical portions can approach to allow said tool to come out of the surgical device; wherein said coupling system comprises a rotational engaging assembly comprising a sleeve containing said rod inside, said rotational engaging assembly protruding from said gripping portion along said main development direction of the tool up to a free end thereof which has a polygonal internal profile which can be engaged with said surgical device.

2. The surgical tool according to claim 1, wherein said coupling system comprises a nut screw adapted to interact on a threaded portion of said central clutch to promote the axial translation thereof.

3. The surgical tool according to claim 2, wherein said nut screw is integral with said gripping portion.

4. The surgical tool according to claim 1, wherein the tool comprises movement means which are directly active on said central clutch to axially rotate the central clutch.

5. The surgical tool according to claim 4, wherein said movement means comprise a driving handwheel which is integral with said central clutch.

6. A kit for positioning a surgical device, the kit comprising:
    the surgical tool according to claim 1; and
    at least one surgical device provided with a head which can be coupled to the coupling system of said surgical tool.

7. The kit according to claim 6, wherein said head has a polygonal external profile, adapted to be engaged with the polygonal internal profile of the rotational engaging assembly of the coupling system.

8. The kit according to claim 6, wherein the surgical device has a stem with a first and a second external thread.

9. The kit according to claim 8, wherein said first and second external threads have mutually different pitches.

* * * * *